United States Patent [19]

Panoz et al.

[11] Patent Number: 4,609,542

[45] Date of Patent: Sep. 2, 1986

[54] NEW PHARMACEUTICAL FORMS FOR ADMINISTRATION OF MEDICAMENTS BY ORAL ROUTE, WITH PROGRAMMED RELEASE

[75] Inventors: Donald E. Panoz, Dublin, Ireland; Gilbert Corneille, Paris, France

[73] Assignee: Elan Corporation, P.L.C., Athlone, Ireland

[21] Appl. No.: 750,980

[22] Filed: Jul. 1, 1985

Related U.S. Application Data

[63] Continuation of Ser. No. 434,269, Sep. 30, 1982, abandoned, which is a continuation of Ser. No. 104,985, Dec. 18, 1979, abandoned.

[30] Foreign Application Priority Data

| Dec. 22, 1978 | [FR] | France | 78 36084 |
| Apr. 2, 1979 | [FR] | France | 79 08180 |
| Apr. 2, 1979 | [FR] | France | 79 08181 |
| Dec. 7, 1979 | [FR] | France | 79 30041 |

[51] Int. Cl.⁴ .................. A61K 9/22; A61K 9/24; A61K 9/26; A61K 31/43
[52] U.S. Cl. ...................... 424/19; 424/20; 424/22; 424/32; 424/33; 424/38; 514/192; 514/197
[58] Field of Search .................. 424/19–22, 424/32, 33, 38; 514/192, 197

[56] References Cited

U.S. PATENT DOCUMENTS

| 2,702,264 | 2/1955 | Klaul | 424/33 |
| 2,809,917 | 10/1957 | Hermelin | 424/34 |
| 2,809,918 | 10/1957 | Hermelin | 167/82 |
| 2,853,420 | 9/1958 | Lowey | 424/35 |
| 2,897,122 | 7/1959 | Millar | 424/33 |
| 2,918,411 | 12/1959 | Hill | 424/80 |
| 2,953,497 | 9/1960 | Press | 424/34 |
| 2,991,226 | 7/1961 | Millar et al. | 424/33 |
| 2,993,837 | 7/1961 | Millar et al. | 424/33 |
| 2,996,431 | 8/1961 | Barry | 424/33 |
| 3,044,938 | 7/1962 | Halley | 424/33 |
| 3,080,294 | 3/1963 | Shepard | 424/20 |
| 3,081,233 | 3/1963 | Enz et al | 424/33 |
| 3,096,248 | 7/1963 | Rudzki | 424/32 |
| 3,102,845 | 9/1963 | Fennell | 424/22 |

(List continued on next page.)

FOREIGN PATENT DOCUMENTS

| 2421273 | 11/1974 | Fed. Rep. of Germany . |
| 1347413 | 11/1963 | France . |
| 2051524 | 4/1971 | France . |
| 2226992 | 11/1974 | France . |
| 2312774 | 12/1976 | France . |
| 2353285 | 12/1977 | France . |
| 2368272 | 5/1978 | France . |
| 2390959 | 12/1978 | France . |
| 45-29314 | 9/1970 | Japan . |
| 785262 | 10/1957 | United Kingdom . |
| 831907 | 4/1960 | United Kingdom . |
| 927218 | 5/1963 | United Kingdom . |
| 934089 | 8/1963 | United Kingdom . |
| 1204580 | 9/1970 | United Kingdom . |
| 1297476 | 11/1972 | United Kingdom . |
| 1367608 | 9/1974 | United Kingdom . |
| 1443923 | 7/1976 | United Kingdom . |

OTHER PUBLICATIONS

Lachman et al, The Theory and Practice of Industrial Pharmacy 2nd Ed. (1976) Lea & Febiger, Phila., Pa., pp. 296–358, 439–465.

(List continued on next page.)

*Primary Examiner*—Shep K. Rose
*Attorney, Agent, or Firm*—Hubbard, Thurman, Turner & Tucker

[57] ABSTRACT

The present invention relates to a new pharmaceutical form for oral use in the nature of delayed action and controlled absorption medicaments.

This form comprises an association of miniaturized granules obtained by high to very high compression: (a) with pH control agents, (b) coated with excipients determining the slow penetration of digestive and/or (c) coated with a very thin layer of lipids. These miniaturized granules may contain glucose, nay have pH control agents with different solubilities, and may be in the form of miniaturized granules with a pH gradient.

2 Claims, 10 Drawing Figures

U.S. PATENT DOCUMENTS

| | | | |
|---|---|---|---|
| 3,115,441 | 12/1963 | Hermelin | 424/22 |
| 3,166,476 | 1/1965 | Lowey | 424/21 |
| 3,325,365 | 6/1967 | Hotko et al. | 424/33 |
| 3,344,029 | 9/1967 | Berger | 424/19 |
| 3,538,214 | 11/1970 | Polli et al. | 424/19 |
| 3,629,393 | 12/1971 | Nakamoto et al. | 424/22 |
| 3,725,470 | 4/1973 | Bretschneider et al. | 260/519 |
| 3,728,445 | 4/1973 | Bardani | 424/22 |
| 3,828,106 | 8/1974 | Rudel | 424/239 |
| 3,954,959 | 5/1976 | Pederson | 424/21 |
| 3,961,004 | 6/1976 | Nasir et al. | 264/115 |
| 3,965,256 | 6/1976 | Leslie | 424/22 |
| 4,016,254 | 4/1977 | Seager | 424/271 |
| 4,016,744 | 4/1977 | Williams | 73/11 |
| 4,025,613 | 5/1977 | Guy et al. | 424/21 |
| 4,113,816 | 9/1978 | Estevenel et al. | 264/113 |
| 4,121,289 | 10/1978 | Stiel | 364/552 |
| 4,137,300 | 1/1979 | Sheth et al. | 424/21 |
| 4,177,254 | 12/1979 | Khan et al. | 424/271 |
| 4,267,138 | 5/1981 | Dobo et al. | 264/117 |
| 4,289,795 | 9/1981 | Bogentoft et al. | 427/3 |
| 4,321,253 | 3/1982 | Beatty | 424/35 |
| 4,341,759 | 7/1982 | Bogentoft et al. | 424/19 |

OTHER PUBLICATIONS

Patel et al, J. Pharm. Sci. 64(5):869–872, May 1975, Oral Absorption Efficiency of Acid-Labile Antibiotics from Lipid-Drug Delivery Systems.

Patel, S. P., Diss. Abstr. Int. B(1975) 35(8):4013–4014, The Use of Cholesterol, Cholesteryl Acetate and β-Sitosterol as Specialized Lipid Carriers for Oral and Implantation Depot Therapy.

Patel, S. P. et al, Drug Develop. Commun. 2(6):465–494 (1976), The Dissolution Rate and the Oral Absorption Efficiency of Selected Salicylates from Lipid-Drug Delivery Systems.

Kim et al, J. Pharm. Sci. 66(11):1536–1540, Nov. 1977, Surface Tension Lowering and Dissolution Rate of Hydrocortisone from Solid Solutions of Selected N-Acyl Esters of Cholesterol.

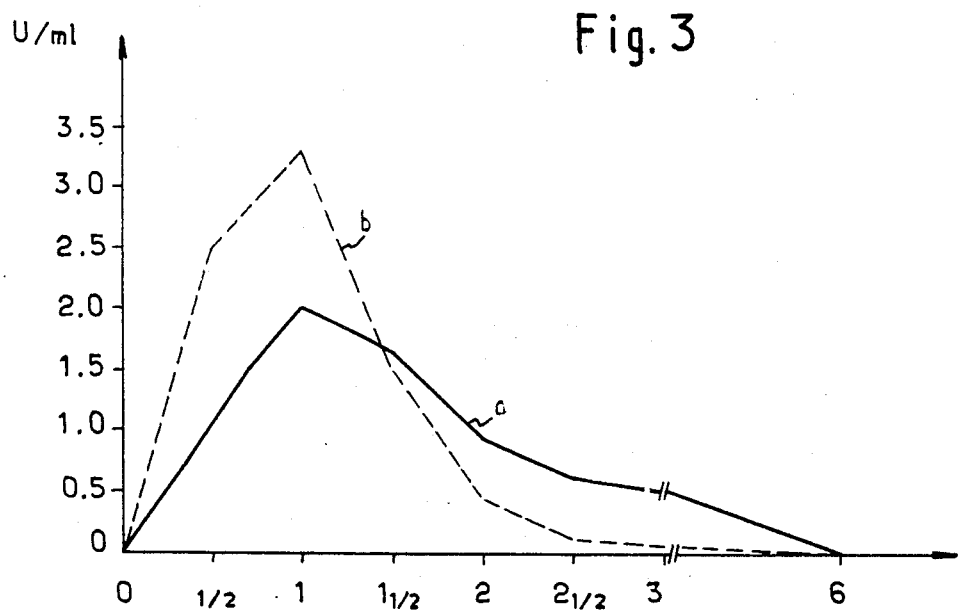
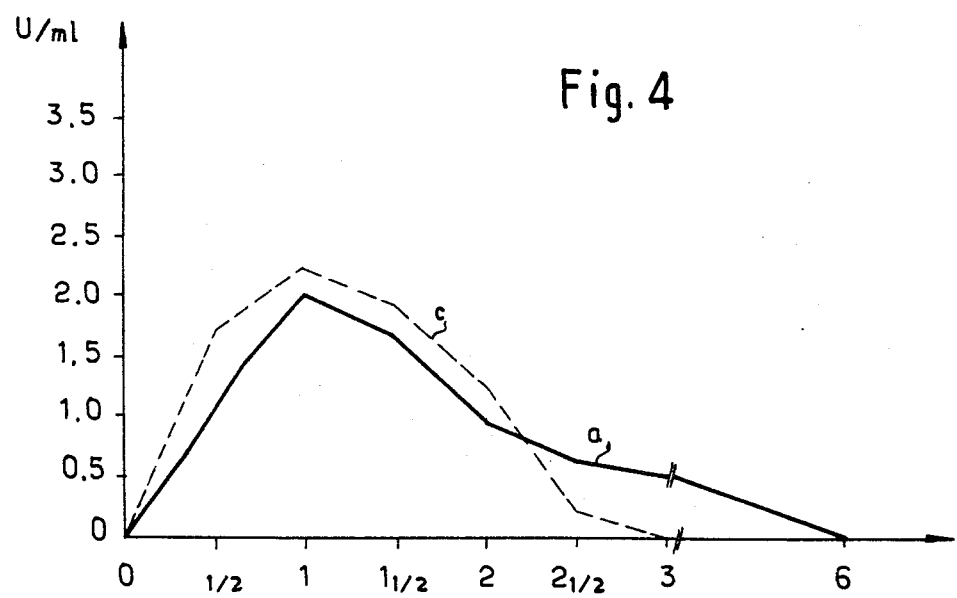

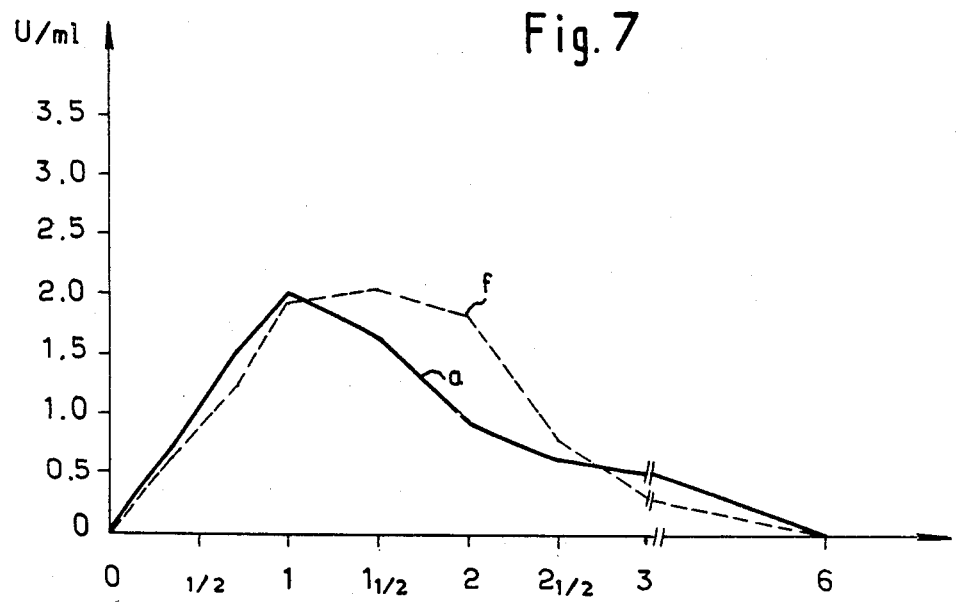
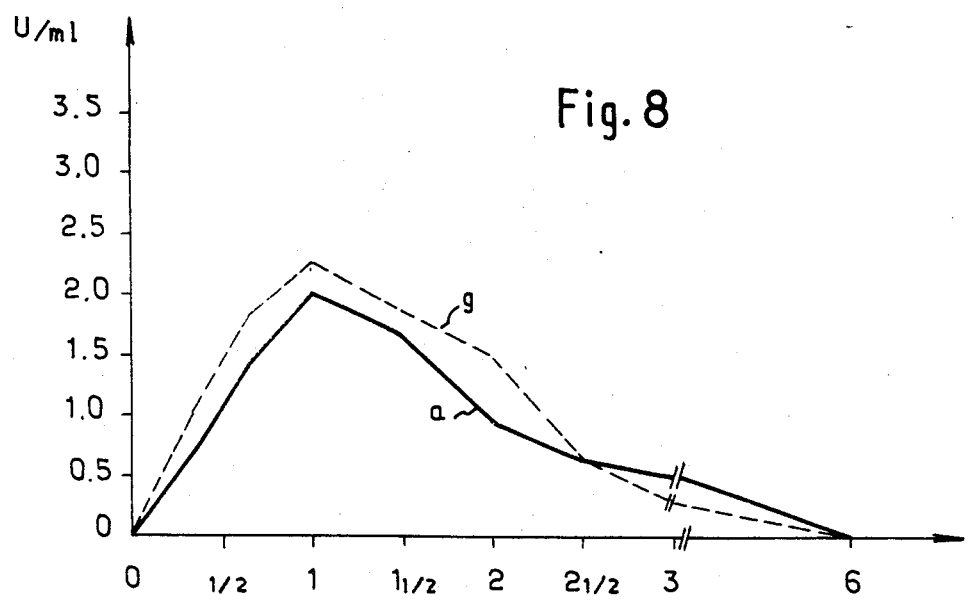

NEW PHARMACEUTICAL FORMS FOR ADMINISTRATION OF MEDICAMENTS BY ORAL ROUTE, WITH PROGRAMMED RELEASE

This application is a continuation of application Ser. No. 434,269, filed Sept. 30, 1982, now abandoned, which in turn is a continuation-in-part of application Ser. No. 104,985, filed Dec. 18, 1979, now abandoned.

FIELD OF THE INVENTION

The present invention relates to new pharmaceutical forms for administration of medicaments by oral route. It relates more particularly to pharmaceutical forms of programmed release medicaments, adjustable as desired, allowing the diffusion of the medicaments which they contain, according to perfectly predetermined kinetics.

DESCRIPTION OF THE PRIOR ART

Though the pharmaceutical industry may have at its disposal an imposing arsenal of drugs and medicaments, it is still at the trial and error stage insofar as the best method of administration, the mode and mechanism of action of the medicaments in the human body, the fate of the medicaments in the organism and the determination of the efficient quantities of medicaments which should be administered, are concerned. If we add to that the very different characteristics of the active constituents administered, some of which are absorbed very quickly, others very slowly, incompletely or unevenly, yet others of which are more or less soluble, or have a tendency to hydrolyze or to decompose or, worse still, to decompose while leaving a more or less toxic residue, and yet others which are incompatible or aggressive as regards certain parts of the gastro-intestinal tract, we can readily understand that the form of administration of the medicament is as important as the administered medicaments themselves.

We must add to that the fact the absorption of certain medicaments can only take place in a perfectly determined environment, particularly insofar as the pH, the solvents, the concentration, etc . . . are concerned. Others, finally, can only be absorbed at certain precise points of the intestinal tract, particularly, for example, in certain parts of the duodenum or of the small intestine, etc. It is therefore understandable that the pharmaceutical industry has sought for a long time to resolve the problem of the absorption of medicaments, either by acting on the duration of action of the medicaments, or by controlling and adjusting their release. Thus it is that many so-called delayed forms have arisen, among which are known medicinal forms coated with gastro-soluble, gastro-resistant or entero-soluble protecting layers; —coated medicinal forms with a porous matrix and provided with a thin permeable coating; —multilayer pharmaceutical forms, i.e. tablets in which the medicinal substances are distributed into different layers, superposed by successive compressions, optionally separated by layers of excipients; —microcapsules formed by elementary particles of small dimensions coated with a protecting film; —tablets containing in their mass delayed-release microcapsules; —pharmaceutical forms comprising spherical particles provided with dialysis membranes; —capsules filled with tablets containing the active constituent(s) coated with layers of different ingredients of different thicknesses.

The diversity of the solutions proposed in the prior art allows a definite percentage of disintegration in the stomach, another in the duodenum, and yet another in the small intestine, etc. to be obtained.

All the pharmaceutical forms recommended in the prior art give, when plotting the curve of concentration of the medicament in the blood with respect to the time, one or more peaks which are more or less pronounced, one or more troughs which are more or less pronounced, but, in no case, an even plateau.

Other factors have also been worked on to increase and potentialize the activity of the medicament (especially with a view to reducing the doses thereof), as for example: the micronization of the active ingredient, which increases considerably its specific area; —the addition of a lipid, which results in a potentialization of the order of 20%, but at the price of an addition of a weight of lipid of the order of 600% in relation to that of the active ingredient, which makes it very difficult to take orally.

GENERAL DESCRIPTION OF THE INVENTION

The present invention has therefore as an aim to provide a new pharmaceutical delayed form for oral use which answers better the requirements of practice than the previously known delayed forms, particularly in that it enables either perfect absorption curves to be obtained, whatever the characteristic of the active ingredient (frail medicaments, slow or rapid in absorption, etc.), and/or absorption curves with preadjusted and predetermined kinetics, while considerably potentializing the therapeutic action of the medicament and while considerably reducing the volume of the pharmaceutical presentation to be swallowed.

The present invention has for its object a new pharmaceutical form of medicaments for oral use, with selectively adjustable programmed release and controlled absorption, characterized in that it comprises an association defined by the following characteristics:

(a) miniaturized granules obtained by high to very high compression having a central core surrounded by several layers containing a mixture of one or more active ingredients with an active excipient containing a physiologically active neutralization agent for controlling the pH, the layers containing the active ingredients being separated from each other by layers of excipient which determine the slow penetration of the digestive and alimentary liquids, (b) miniaturized granules obtained by high to very high compression containing one or more active ingredients coated with excipients determining the slow penetration of the digestive and alimentary liquids, (c) miniaturized granules containing one or more active ingredients, obtained by high to very high compression, coated with a very thin layer of lipids present in a ratio of 5 to 30% with respect to the active ingredient(s), the proportion of each of the types of miniaturized granules defined under (a), (b) and (c) being able to vary from 0 to 100% according to the desired absorption curve of the medicament associated with said pharmaceutical form, it being understood that (a), (b) and (c) cannot be zero at the same time and must total 100%.

According to an advantageous embodiment of the subject of the invention, the compression is effected under a pressure equal to or greater than 10 tons.

The use of these very high pressures allows the volume of the medicinal preparation to be considerably reduced and the quantity of the protecting lipids to be considerably reduced (of the order of $10^2$), while obtaining a potentialization greater than that of the pharmaceutical preparations known up to present.

According to another advantageous embodiment of the subject of the invention, the size of the miniaturized granules is between 0.2 and 2.0 mm in diameter.

According to another advantageous embodiment of the subject of the invention, the excipient containing the medicament for miniaturized granules of type (a), is composed of one or two substances chosen from the group which comprises polyvinylpyrrolidone, cellulose, ethylcellulose, the methacrylates, the acetophthalates and shellac, each layer being able to comprise identical or different excipients provided that they belong to the group mentioned above.

According to a particular procedure of this embodiment, the pH control agent is chosen from the pharmaceutically acceptable organic acids soluble in alcohol and/or in chloroform and/or in ether and/or in acetone and/or in water, when it is desired to lower the pH value at the moment of discharge of the medicament, or from the alkaline carbonates and bicarbonates, or the pharmaceutically acceptable alkaline salts of weak organic acids and/or the pharmaceutically compatible organic bases soluble in alcohol and/or in water, when it is desired to raise the pH value during discharge of the medicament, provided that the pH control agent is soluble in the same solvent as the active ingredient(s).

According to another embodiment of the subject of the invention, the excipient separating the layers which contain the medicament, for the miniaturized granules of type (a), or which coat the miniaturized granules of type (b), or are mixed with the active ingredient for the miniaturized granules of type (c), is also composed of one or two substances chosen from the group comprising polyvinylpyrrolidone, cellulose, ethylcellulose, the methacrylates, the acetophthalates and shellac.

According to another embodiment of the subject of the invention, the pharmaceutically acceptable lipid used for coating the miniaturized granules of type (c) is soluble in the same solvents as the active ingredient(s).

According to a preferred embodiment of the present invention, the new pharmaceutical form of medicament for oral administration with selectively adjustable programmed release and controlled absorption, comprises:

(a) granulated highly compressed pulverized particles obtained by high to very high compression at a pressure equal to 15 tons and thereafter grinding said particles having a diameter between 0.2 and 2 mm, of an active ingredient comprising potassium phenoxymethyl-penicillin with an active excipient containing a physiologically active neutralization agent for controlling the pH, said neutralization agent comprising sodium citrate;

(b) granulated highly compressed pulverized particles obtained by high to very high compression at a pressure of 15 tons and thereafter grinding said particles having a diameter between 0.2 and 2 mm, containing an active ingredient comprising potassium phenoxymethylpenicillin coated with an excipient determining the slow penetration of the digestive and alimentary liquids, said excipient including polyvinyl-acetate-phthalate;

(c) granulated highly compressed pulverized particles containing an active ingredient comprising potassium phenoxymethylpenicillin, obtained by high to very high compression at a pressure of 15 tons and thereafter grinding said particles having a diameter between 0.2 and 2 mm, coated with a very thin layer of lipids, compressing cholesteryl acetate-chloroform in a ratio of 1:2 (weight:volume), said lipids being present at a rate of 5 to 30% in relation to the active ingredients, the proportions by weight of each of particles (a), (b) and (c) being 1:1:1.

Studies and experiments on the bio-availability of medicaments ingested by oral route, have shown even more clearly the importance of the physical and physico-chemical factors whose influence on the bio-availability of the medicaments and, consequently; on the very treatment of the illness, is at least as important as the chemical nature of the molecule itself. These studies have shown the influence of factors such as: the solubility, the pKa, the crystalline or amorphous state, the crystallization or solvation water, the dimension of the particles of the active ingredient and its specific area, the property of compressibility of the particles of active constituents, the influence of pH of the medium, the importance of the additives and of the excipients associated with the active constituent, etc.

It is also advisable, and this so as to have an optimum therapeutic effect, or "therapeutic ratio", to adapt all these factors not only for each chemical molecule, but also according to the therapeutic effect desired. In fact, the procedure will be different in the case of a hypnotic, for example, where the speed of absorption and the maximum concentration (the peak of the absorption curve) are more important than the total amount absorbed. On the other hand, the same compound will have another pharmaceutical formulation if it is the sedative effect which is sought, in which case it is the total amount absorbed which is especially important. Similarly, for example, in the case of a bacterial antibiotic, it is sometimes preferable to have intermittently high absorption peaks, whereas the bacteriostatic compounds require on the contrary blood levels always above the inhibitory minimum concentration with respect to the microorganism to be fought.

In accordance with the invention, the control agent of the pH is composed of several pharmaceutically compatible organic acids having different solubilities.

By choosing neutralization and pH control agents having different solubilities, a sort of neutralization-delay phenomenon is created. Because of the different solubilities, these pH control agents relay each other while the active ingredient travels along the gastrointestinal tract and thus maintain throughout this tract optimum absorption conditions.

In accordance with an advantageous embodiment of the subject of the invention, the pH control agent is formed by a mixture of fumaric and/or tartaric and/or citric acid.

In accordance with the invention, the amount of acid which forms the pH control agent, in relation to the amount of the active ingredient, increases from the central core to the periphery of the miniaturized granule which thus forms a miniaturized granule with a pH gradient.

BRIEF DESCRIPTION OF THE DRAWINGS

One of the aims of the present invention is to better define the influence of a factor as important as the pH of the medium; in fact, this is not constant and changes along the whole of the gastro-intestinal tract, and the medicament absorbed orally must consequently affront the environmental medium whose pH varies. The possibility of controlling the release of the active ingredient all along the path of the medicament in the gastro-intestinal tract presupposes that the solubility of the medicament can be controlled at each instant of this progression. If one examines the solubility of most of the commercially available medicaments, one can see that it varies considerably as a function of the pH. Thus it is that FIG. 1 shows the solubility of two commercial medicaments, i.e. vincamine hydrochlorate (curves $v_1$, $v_2$ and $v_3$) and dipyridamole (curves $d_1$, $d_2$ and $d_3$) as a function of the pH.

We can see clearly from this figure that the dissolution of the vincamine at pH 1.5 (curve $v_1$) is practically complete at the end of 30 minutes, whereas it only takes place after an hour at pH 3.0 (curve $v_2$), and that it scarcely reaches 45% after 6 hours at pH 6 (curve $v_3$). The case is even more serious for dipyridamole: at pH 1.5 (curve $d_1$), the dissolution is complete after half an hour, it is 90% after 2½ hours at pH 3 (curve $d_2$), and it never exceeds 15% at pH 6 (curve $d_3$).

By operating thus in accordance with the present invention, we succeed in mastering almost perfectly the diffusion kinetics of a medicament in the gastro-intestinal tract.

Figure 1:
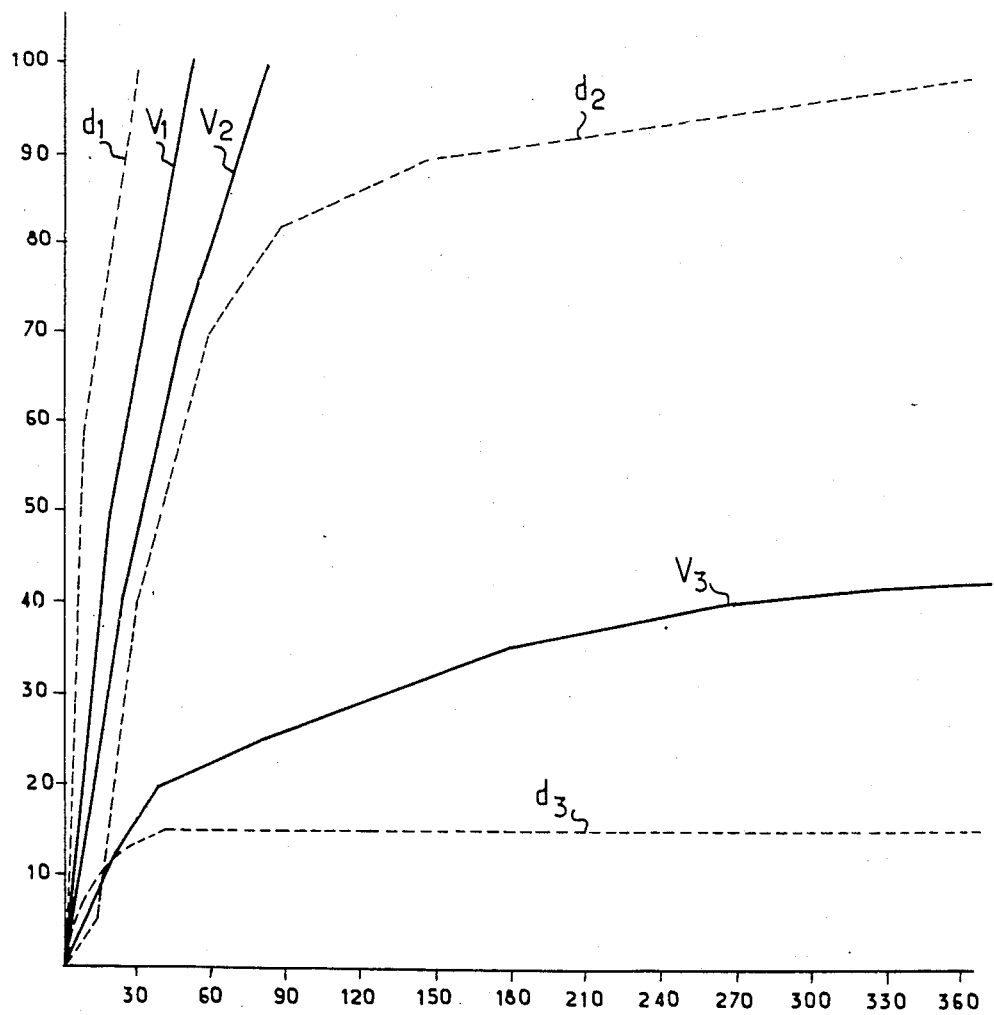
Figure 2:
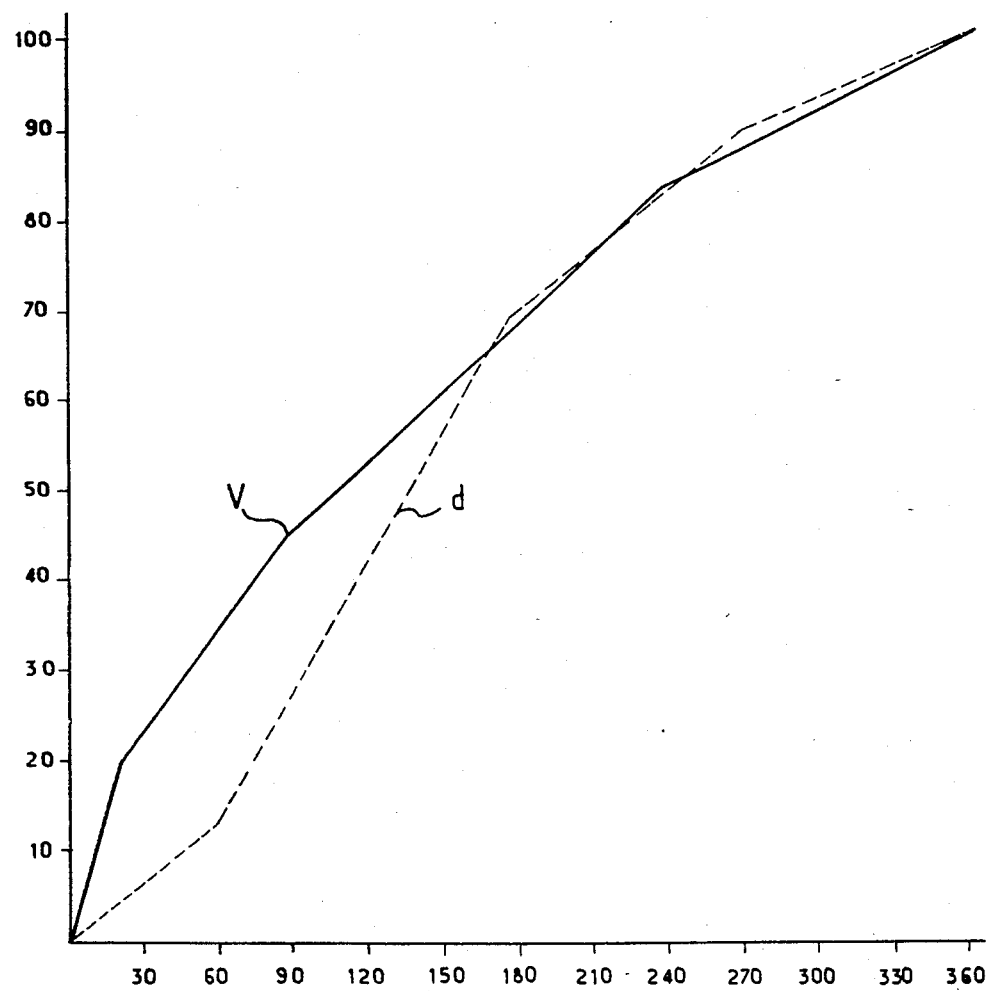

FIG. 2 shows—by way of non-limiting example—the solubility of the same two medicaments as those mentioned in FIG. 1, but prepared in accordance with the present invention. The dissolution curve is identical whatever the pH (1.5–3.0 or 6) and this not only for vincamine (curve v) but also for dipyridamole (curve d). The the same results have been achieved with a large number of medicaments and particularly with diazepam, cephalexin, cimetidin, cephalotin, methyldopa, cephazolin, propanolol, indomethacin, ibuprofen, doxycyclin, amoxycillin, furosemide, dipyridamole, spironolactone, erythromycin, gentamicin, diclofenac, glibenclamide, althiaside, naproxen, propoxyphene, allopurinol, sulfamethoxazole, ampicillin, prosultiame, lincomycin, betamethasone, troleandomycin, vincamine, clonidine, glafenine, clometacine, disopyramide, sulpiride, oxyphenbutazone, chlorazepate, cephalosporin, rifamycin and sulindac.

According to another advantageous embodiment of the subject of the invention, the acid/active ingredient ratio varies from 1.5 to 5/1 (central core) to 0.2–0.5/1 (peripheral layer).

In accordance with the invention, the granules may moreover contain glucose and/or derivatives thereof.

It has been discovered surprisingly that the addition of glucose and its derivatives increases the intestinal absorption speed; thus, the quantity of this product added can be adjusted according to the desired absorption curves.

According to an advantageous embodiment of the subject of the invention, the amount of glucose and/or its derivatives used is between 1 and 25% by weight in relation to the total weight of the composition.

The present invention also has as subject matter a process for preparing the new pharmaceutical form in accordance with the invention, characterized in that first of all the three types of miniaturized granules are prepared separately:

I. type (a) (with controlled pH)

by mixing the active ingredient(s), with a disintegrator when required,
by granulating this mixture with a pH control agent solution in a proportion of 0.05 to 1% with respect to the active ingredient,
by then granulating with the chosen excipients,
by treating the wet granulate obtained, in an oscillating granulator,
by drying the granules at a temperature between 30° and 45° C.,
by then compressing at a pressure equal to or greater than 10 tons,
by then grinding and sifting, and collecting the particles whose size is between 0.2 and 2.0 mm in diameter, the finest and coarsest particles being recycled.
then by coating with the chosen excipients, 2. type (b) miniaturized compressed granules)

by mixing the active ingredient(s) with a disintegrator when required,
by granulating this mixture with the chosen excipient,
by treating the wet granulate in an oscillating granulator,
by drying the granules at a temperature between 30° and 45° C.,
by compressing at a pressure equal to or greater than 10 tons,
by grinding and sifting the compressed material and collecting the particles whose size is between 0.2 and 2.0 mm in diameter, the finest and coarsest particles being recycled,
by coating with the chosen excipient, 3. type (c) (miniaturized lipidized granules)

by mixing the active ingredient(s) with a disingrator when required,
by granulating this mixture with a lipid solution, the proportion of the lipid added varying between 5 and 30% by weight of the active ingredient,
by then mixing with a solution containing the chosen excipient,
by treating the wet granulate in an oscillating granulator,
by drying the granules at a temperature between 30° and 45° C.,
by compressing at a pressure equal to or greater than 10 tons,
by grinding and sifting the compressed material and collecting the particles whose size is between 0.2 and 2.0 mm in diameter, the finest and coarsest particles being recycled,
by coating with the chosen excipient, then, after having separately prepared the three types of miniaturized granules, they are mixed in the desired proportions.

Besides the arrangements described above, the invention comprises still other arrangements which will become clear from the following description.

The invention relates particularly to new pharmaceutical forms in accordance with the preceding arrangements, as well as the means for accomplishing them and for implementing the processes for manufacturing these new forms, as well as the medicaments presented in these galenical forms.

The invention will be better understood by means of the complement of description which follows, which refers to examples of manufacture as well as to clinical tests for determining the level of medicament in the blood with respect to the percentage of the different types of miniaturized granules constituting the pharmaceutical form of administration of the medicament.

It will be however readily understood that these examples and these clinical tests are given solely by way of illustration of the subject matter of the invention, of which they constitute in no wise a limitation.

EXAMPLES OF PREPARATION

EXAMPLE 1

1.110 kg of potassium phenoxymethylpenicillin is mixed with 0.050 kg of maize starch and 0.1 kg of sodium citrate. This mixture is then granulated with a solution of 5% polyvinylpyrrolidone in 0.25 l of isopropanol. This granulate is treated in an oscillating granulator, then dried at 45° C. Compression is then carried out under a pressure of 15 tons in a "KOMERECK" apparatus, then grinding and sifting are carried out in a "FITZPATRICK" type machine, and the particles having a diameter between 0.5 and 1 mm are collected. The particles having a larger or smaller diameter are recycled.

FIG. 3 shows the blood levels dosed respectively after administration of 1,000,000 units of commercial phenoxymethylpenicillin ("Oracilline" tablets) (curve a) and of 1,000,000 units of penicillin contained in the granules obtained in accordance with Example 1 (curve b). The time (in hours) following the administration of the medicament is shown as abscissa and the blood levels (in units of penicillin per ml of blood) as ordinate.

It can be seen from these curves that the level of the medicament in the blood increases much more rapidly and furthermore reaches levels which are greater with the galenical forms of the invention than with commercial penicillins.

Thus, for example, after an hour, the level of penicillin in the blood is 56% greater for the pharmaceutical forms of the invention.

EXAMPLE 2

1.110 kg of potassium phenoxymethylpenicillin is mixed with 0.050 kg of maize starch. A solution of 0.1 kg of sodium citrate is prepared in 0.1 liter of distilled water. Then this solution is added under vigorous stirring to the preceding mixture. Then a solution of 5% polyvinylpyrrolidone in 0.25 l of isopropanol is added and the whole treated in an oscillating granulator, then dried at 45° C. Compression is then carried out under a pressure of 15 tons in the "KOMERECK" apparatus, then grinding and sifting are carried out in a "FITZPATRICK" type machine, and the particles having a diameter between 0.5 and 1 mm are collected, the other particles being recycled upstream of the line. These particles are then coated with a solution containing 30 ml of polyvinyl-acetate-phthalate and 30 g of talc for 1 kg of granules. Finally, drying is carried out at 45° C.

FIG. 4 shows the blood levels dosed after administration of 1,000,000 units of commercial phenoxymethylpenicillin ("Oracilline" tablets), (curve a), and 1,000,000 units of penicillin contained in the granules obtained in accordance with Example 2 (curve c). The time is shown as abscissa and the blood level as ordinate.

In this example, the peak is identical (2 units of penicillin per ml of blood, one hour after administration), but the blood level after administration of the pharmaceutical form according to the invention increases much more rapidly and decreases much more slowly than for the commercial penicillins.

EXAMPLE 3

1.110 kg of potassium phenoxymethylpenicillin is mixed with 0.050 kg of maize starch. This mixture is moistened with a solution of 0.1 kg of cholesteryl acetate in 200 ml of chloroform. This mixture is then granulated with a solution of 5% polyvinylpyrrolidone in 250 ml of isopropyl alcohol. Then it is treated in an oscillating granulator and dried at 45° C. Then compression is carried out under a pressure of 15 tons in a "KOMERECK" type apparatus, then grinding and sifting are carried out in a "FITZPATRICK" type machine while collecting the particles having a diameter between 0.5 and 1 mm. These particles are then coated with 0.35 l per kg of particles, with a solution of cholesteryl-acetate-chloroform 1:2 (weight:volume) then dried at 45° C.

Figure 5:
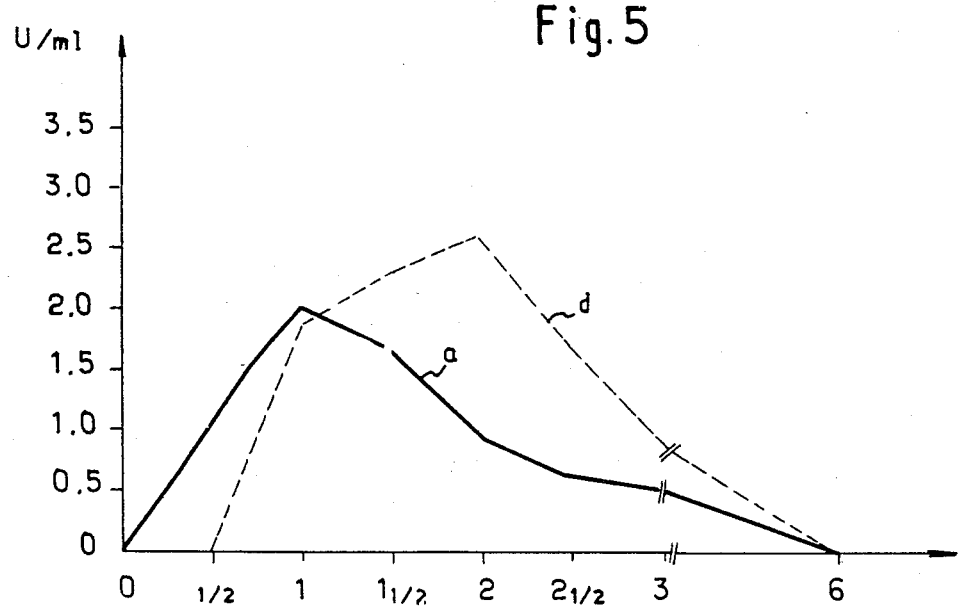

FIG. 5 shows the blood levels dosed after administration of 1,000,000 units of "Oracilline" (curve a) and 1,000,000 units of penicillin contained in the granules obtained according to Example 3 (curve d). The time is shown as abscissa and the blood levels as ordinate. As can be seen in this figure, the trend of curve d has distinctly changed and the duration of action of the medicament is clearly longer in relation to the action of the commercial penicillin.

EXAMPLE 4

The granules obtained from Example 1 are mixed with granules obtained according to Example 3 in the proportion 3:1.

Figure 6:
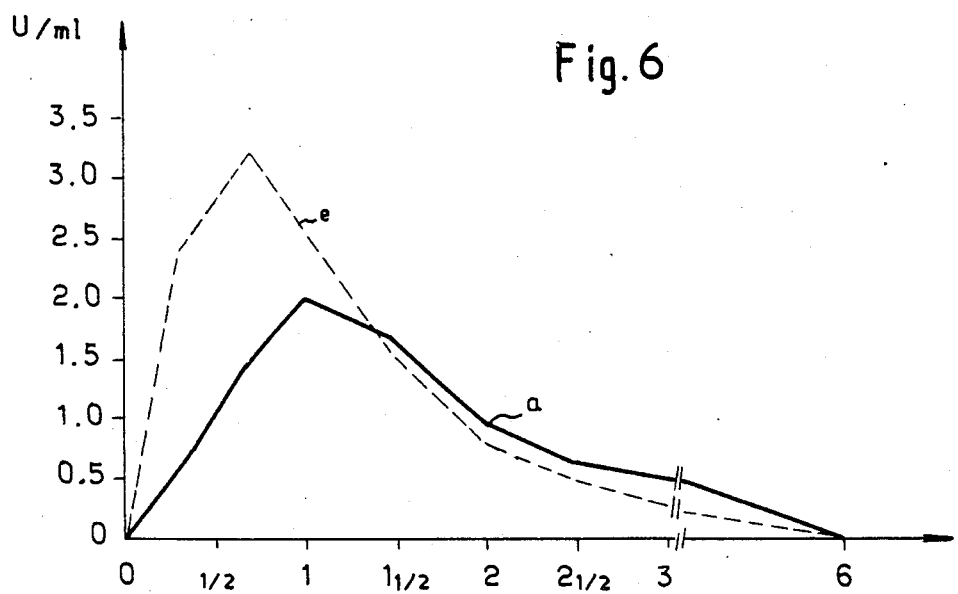

FIG. 6 shows the blood levels obtained, still after administration of 1,000,000 units:
curve a: "Oracilline"
curve e: granules of the invention
In relation to the commercial product, the peak obtained with the granules of the invention is clearly greater and is obtained much more rapidly.

EXAMPLE 5

The granules obtained from Example 2 are mixed with the granules obtained from Example 3, in the proportion of 1:1.

FIG. 7 shows the blood levels obtained:
curve a: after administration of "Oracilline"
curve f: after administration of granules of the invention.

The blood levels are maintained at a high level for a longer time with the products of the invention.

EXAMPLE 6

The three forms of granules obtained from Examples 1, 2 and 3 are mixed in the proportions 1:1:1.

FIG. 8 shows the blood levels obtained:
curve a: after administration of 1,000,000 units of "Oracilline"
curve g: after administration of 1,000,000 units contained in the granules of the invention.

The blood levels of the penicillin administered in the galenical form in accordance with the invention are very considerably greater than the levels obtained after administration of the commercial product.

EXAMPLE 7

1 kg of methyldopa, 0.2 kg of tartaric acid, 0.2 kg of fumaric acid and 0.02 kg of maize starch are mixed, then this mixture is granulated with a 20% solution of polyvinylpyrrolidone in 350 ml of isopropanol. This granulate is treated in an oscillating granulator, then dried at 50° C. Then compression is carried out at a pressure of 15 tons, it is mixed with 0.01 kg of magnesium stearate and compression is again carried out. Then grinding and sifting is carried out in a "FITZPATRICK" type machine and the particles having a diameter between 0.5 and 1 mm are collected, the other particles being recycled upstream of the line.

Figure 9:
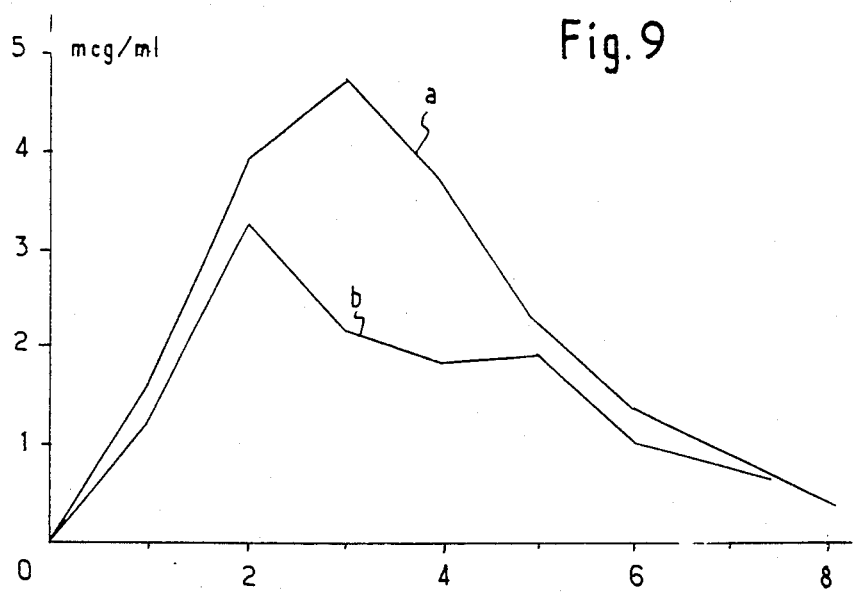

FIG. 9 shows the dosed blood levels after administration of a single dose of 750 mg of active ingredient: curve a shows the blood levels (in mcg per ml) with respect to time (expressed in hours) of microgranules in accordance with the invention, curve b the blood levels obtained after administration of commercial methyldopa tablets ("Aldomet").

The medicament administered in the pharmaceutical form of the invention reaches substantially higher levels (practically the double at the 3rd hour), and this level decreases less rapidly than that obtained with "Aldomet".

EXAMPLE 8

0.5 kg of dipyridamole, 0.25 kg of fumaric acid and 0.01 kg of maize starch are mixed, then this mixture is granulated with 225 ml of a 10% glucose solution. This granulate is treated in an oscillating granulator then dried in a vacuum at 50° C. The dry granulate is then mixed with 0.5 g of magnesium stearate, then compression is carried out under a pressure of 15 tons. Then grinding and sifting are carried out in a "FITZPATRICK" type machine and the particles having a diameter between 0.5 and 1 mm are collected, the other particles being recycled upstream of the line. Then 30 capsules are filled with the above preparation so that their dipyridamole content is 150 mg.

Figure 10:
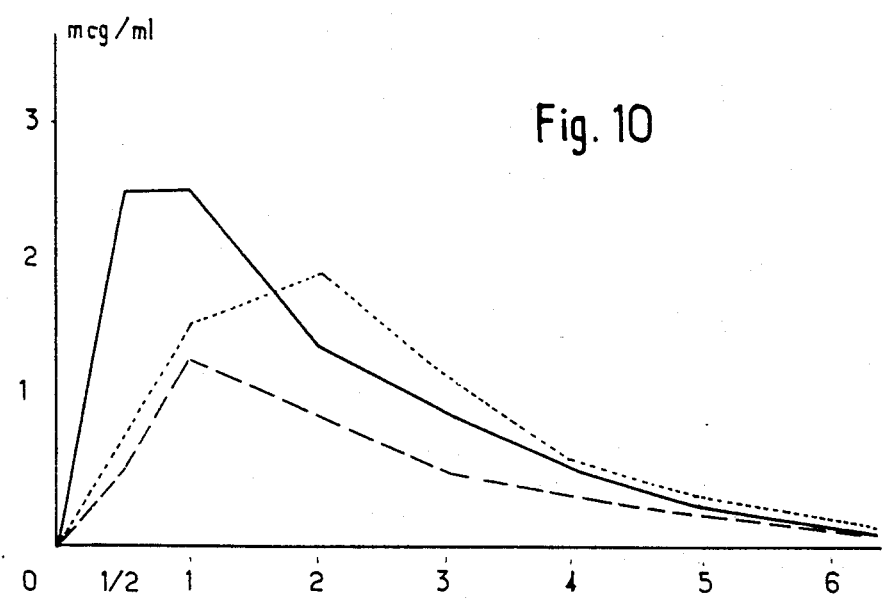

FIG. 10 shows the blood levels dosed after administration of a single dose of 150 mg of dipyridamole:
- curve a shows the blood levels (in mcg of the medicament per ml of blood) with respect to time (expressed in hours) of microgranules obtained under high compression and containing glucose;
- curve b shows the blood levels obtained after administration of the microgranules obtained by high compression, but without glucose;
- curve c shows the blood levels obtained after administration of tablets of commercial dipyridamole ("Persantine").

Thus, for the pharmaceutical form containing glucose in accordance with the present invention, the level of the medicament in the blood is 5 times greater than that obtained after administration of "Persantine". These curves also show that the blood levels also decreases less rapidly for the new pharmaceutical forms in accordance with the invention than for the commercial dipyridamole.

EXAMPLE 9

Preparation of miniaturized granules with pH gradient

1. Preparation of the central core 2.5 kg of vincamine hydrochlorate and 5 kg of fumaric acid are mixed, then this mixture is granulated with a 20% solution of polyvinylpyrrolidone in isopropanol. It is dried at 50° C. Then compression is carried out under a pressure of 15 tons, then grinding and sifting in a "FITZPATRICK" type machine and the particles having a diameter between 0.5 and 0.75 mm are collected, the other particles being recycled upstream of the line.

2. Preparation of the inner layer

An intimate mixture is made of:

0.5 kg of vincamine hydrochlorate
1 kg of fumaric acid
0.05 kg of talc.

The whole is ground so as to have particles with a diameter of about 0.14–0.15 mm.

3. Preparation of the middle layer

An intimate mixture is made of:

0.750 kg of vincamine hydrochlorate
0.325 kg of fumaric acid
0.325 kg of citric acid
0.05 kg of talc The whole is ground so as to have particles with a diameter of about 0.14–0.15 mm.

4. Preparation of the external layer

An intimate mixture is made of:

1 kg of vincamine hydrochlorate
0.5 kg of citric acid
0.05 kg of talc.

The whole is ground so as to have particles with a diameter of about 0.14–0.15 mm.

5. Coating procedure 1.5 kg of cores are placed in the coating tank;
coating with the inner layer is carried out by using a 20% polyvinylpyrrolidone solution;
two layers of hermetizing excipient is applied whose composition is the following:
33% shellac in isopropanol; 20% polyvinylpyrrolidone in isopropanol; isopropanol; talc, in the proportions 1:3:4:4;
then the operation is carried out in the same way with the middle and external layers.

It follows from the preceding description that, whatever the modes of implementation, of embodiment and application adopted, new pharmaceutical forms of medicaments for oral use are obtained, whose release kinetics may be perfectly predetermined, and which enable blood levels to be obtained more uniformly and/or much higher than those obtained with all the pharmaceutical forms at present on the market.

As can be seen from what has preceded, the invention is in no wise limited to those of its modes of implementation, of embodiment and of application which have just been described above in a more explicit manner; it embraces, on the contrary, all the variations thereof which may come to the mind of the man skilled in the art, without departing from the scope or the spirit of the present invention.

What is claimed is:

1. A new pharmaceutical form of medicament for oral administration with selectively adjustable programmed release and controlled absorption, comprising:
    (a) granulated highly compressed pulverized particles obtained by high to very high compression at a pressure equal to 15 tons and thereafter grinding said particles having a diameter between 0.2 and 2 mm, of an active ingredient comprising potassium phenoxymethylpenicillin with an active excipient containing a physiologically active neutralization agent for controlling the pH, said neutralization agent comprising sodium citrate;
    (b) granulated highly compressed pulverized particles obtained by high to a very high compression at a pressure of 15 tons and thereafter grinding said particles having a diameter between 0.2 and 2 mm, containing an active ingredient comprising potassium phenoxymethylpenicillin coated with an excipient determining the slow penetration of the digestive and alimentary liquids, said excipient including polyvinyl-acetate-phthalate;

(c) granulated highly compressed pulverized particles containing an active ingredient comprising potassium phenoxymethylpenicillin, obtained by high to very high compression at a pressure of 15 tons and thereafter grinding said particles having a diameter between 0.2 and 2 mm, coated with a very thin layer of lipids, compressing cholesteryl acetatechloroform in a ratio of 1:2 (weight:volume), said lipids being present at a rate of 5 to 30% in relation to the active ingredients, the proportions by weight of each of particles (a), (b) and (c) being 1:1:1.

2. In a pharmaceutical form of medicament for oral administration with selectively adjustable programmed release and controlled absorption, the improvement comprising:

(a) granulated highly compressed pulverized particles obtained by high to very high compression at a pressure equal to 15 tons and thereafter grinding said particles having a diameter between 0.2 and 2 mm, of an active ingredient comprising potassium phenoxymethylpenicillin with an active excipient containing a physiologically active neutralization agent for controlling the pH, said neutralization agent comprising sodium citrate;

(b) granulated highly compressed pulverized particles obtained by high to a very high compression at a pressure of 15 tons and thereafter grinding said particles having a diameter between 0.2 and 2 mm, containing an active ingredient comprising potassium phenoxymethylpenicillin coated with an excipient determining the slow penetration of the digestive and alimentary liquids, said excipient including polyvinyl-acetate-phthalate;

(c) granulated highly compressed pulverized particles containing an active ingredient comprising potassium phenoxymethylpenicillin, obtained by high to very high compression at a pressure of 15 tons and thereafter grinding said particles having a diameter between 0.2 and 2 mm, coated with a very thin layer of lipids, compressing cholesteryl acetatechloroform in a ratio of 1:2 (weight:volume), said lipids being present at a rate of 5 to 30% in relation to the active ingredients, the proportions by weight of each of particles (a), (b), and (c) being 1:1:1.

* * * * *